Figure 1:
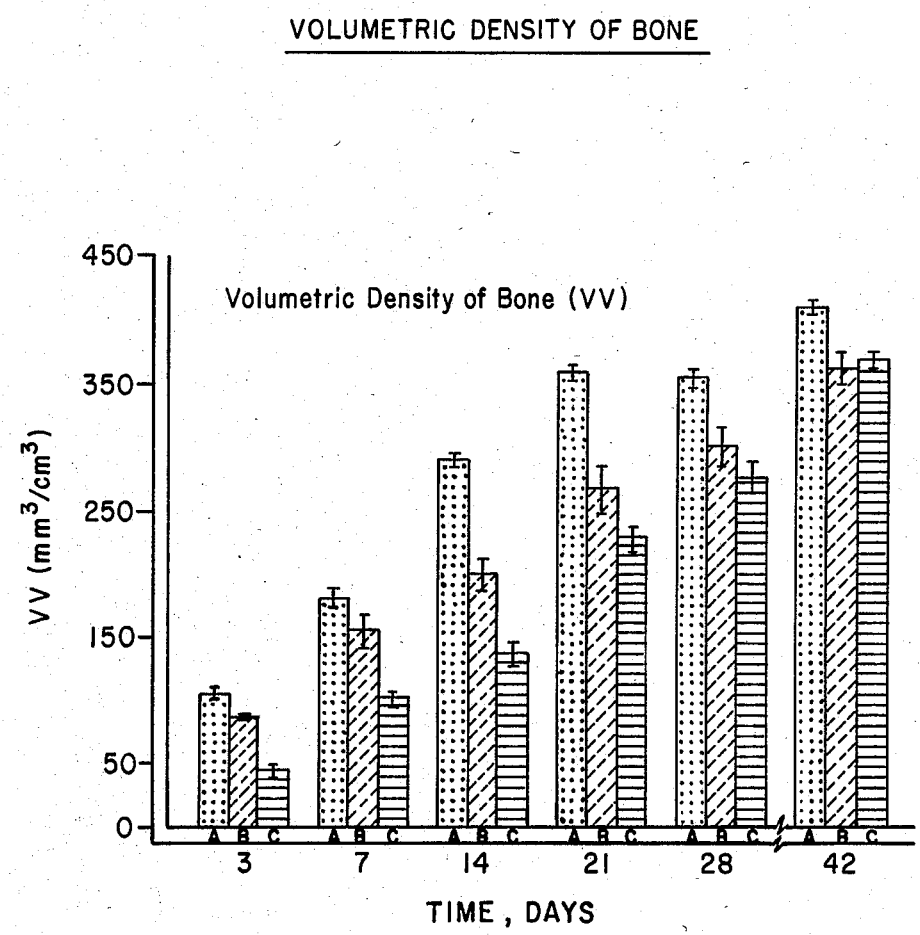
Figure 2:
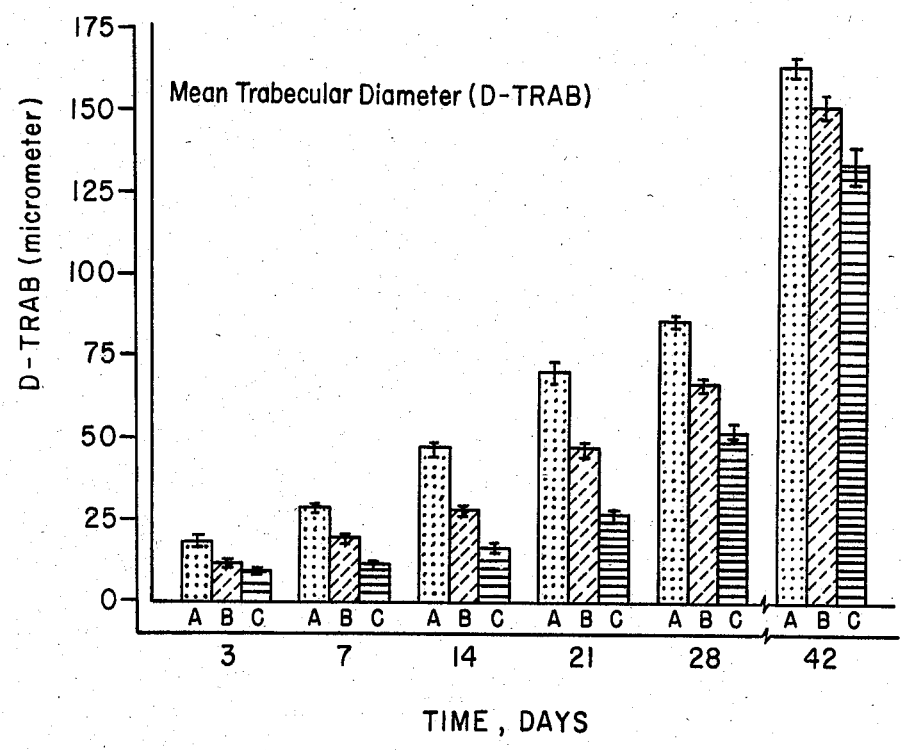
Figure 3:
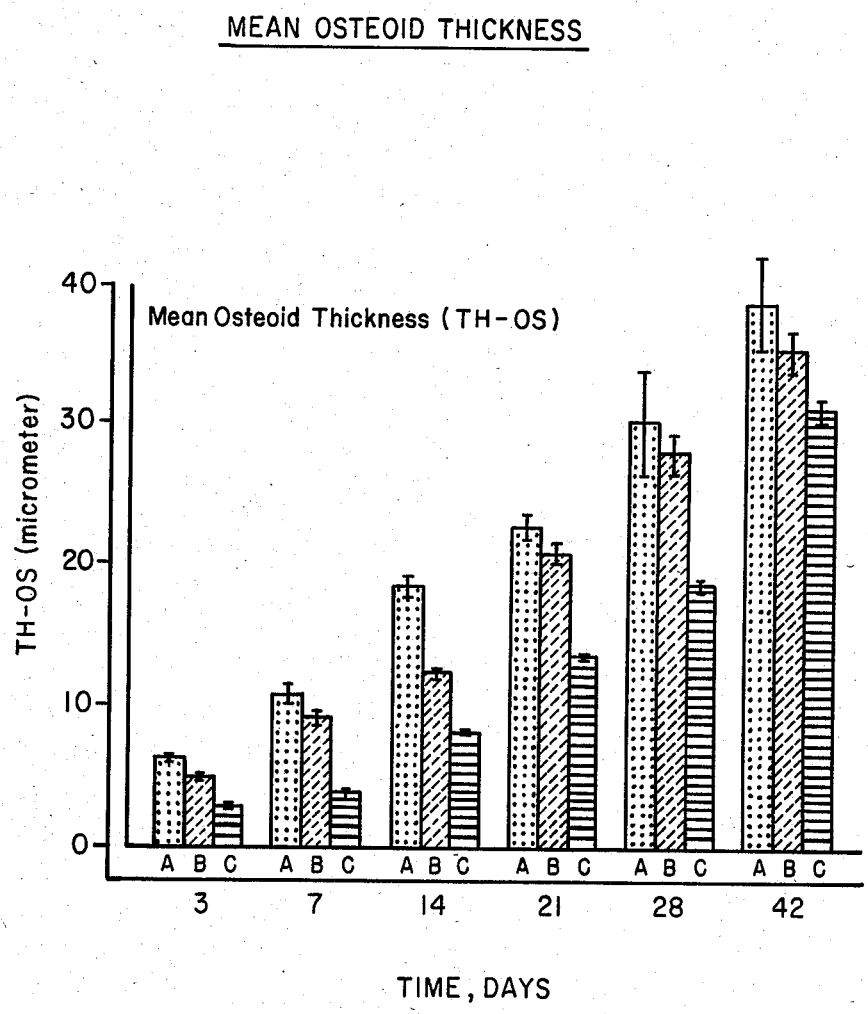
Figure 4:
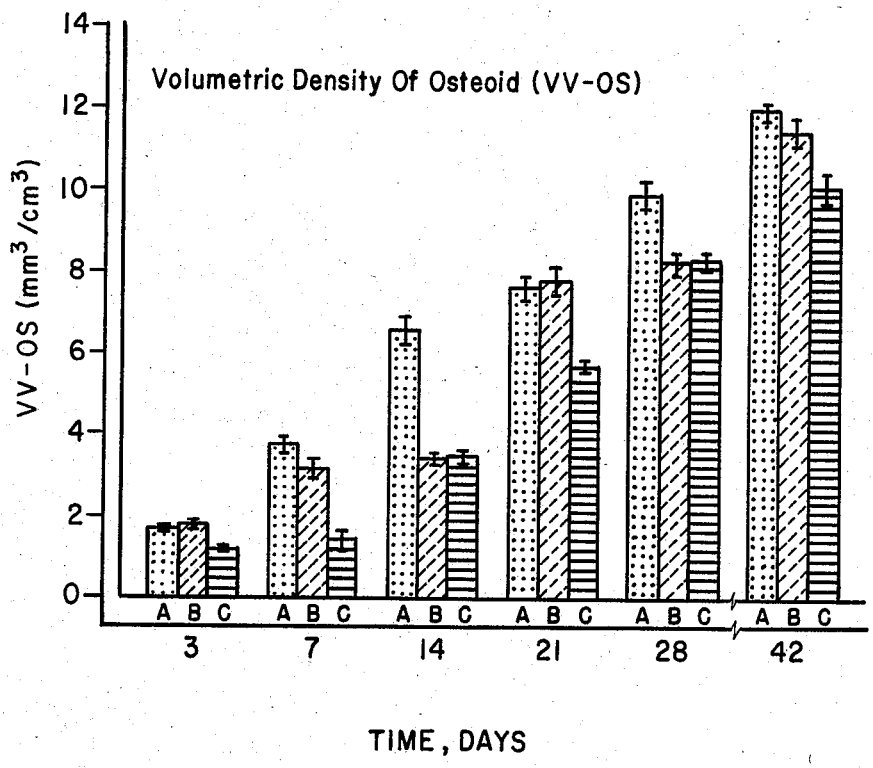
Figure 5:
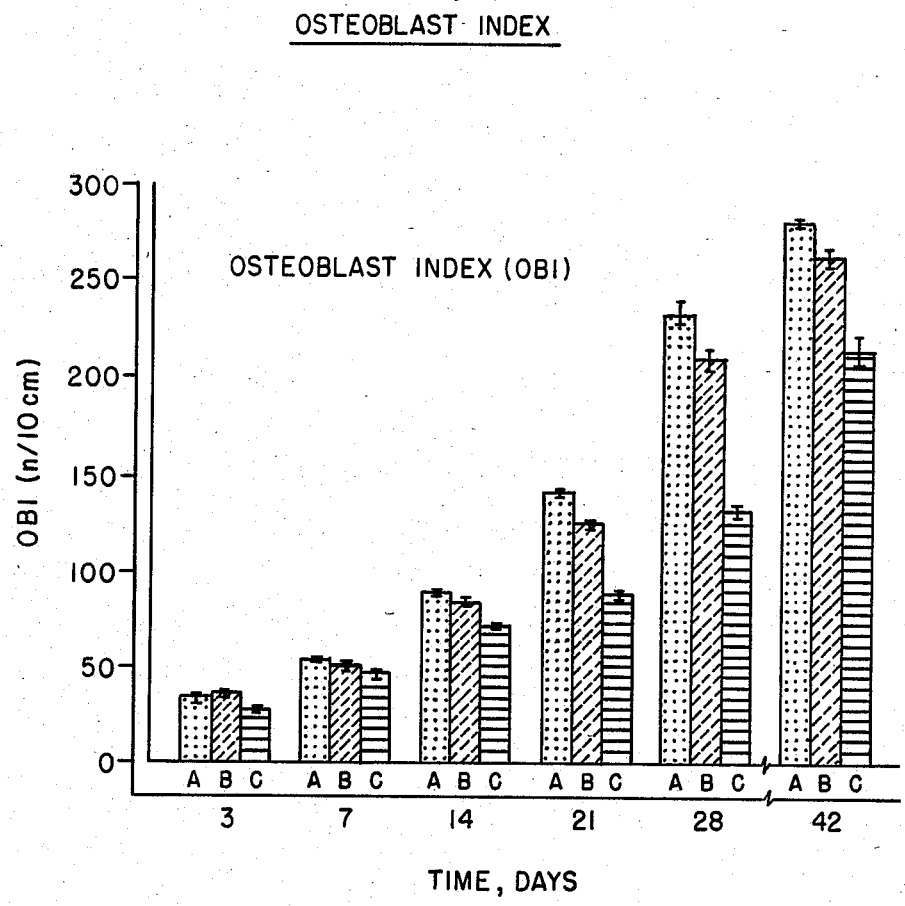
Figures 6, 7:
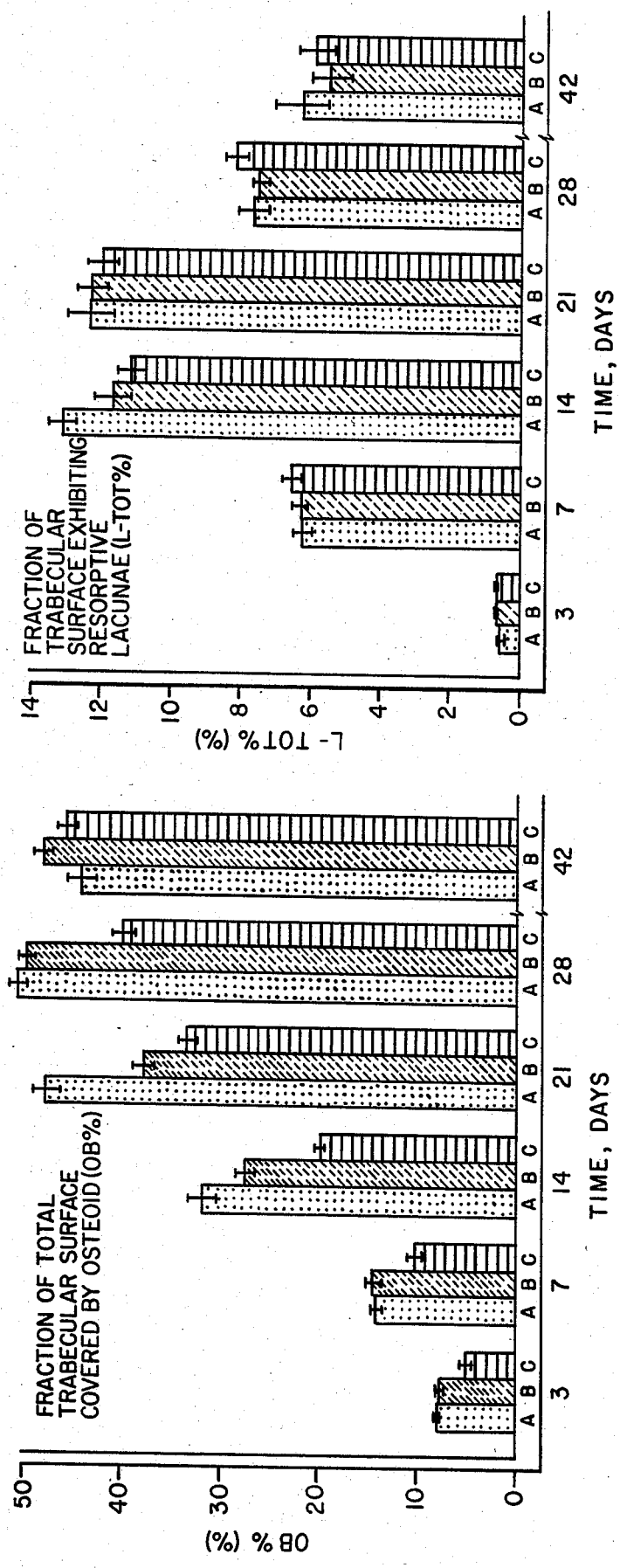

United States Patent [19]

Hollinger

[11] Patent Number: 4,578,384
[45] Date of Patent: Mar. 25, 1986

[54] POLYLACTIC-POLYGLYCOLIC ACIDS COMBINED WITH AN ACIDIC PHOSPHOLIPID-LYSOZYME COMPLEX FOR HEALING OSSEOUS TISSUE

[75] Inventor: Jeffrey O. Hollinger, Glenwood, Md.

[73] Assignee: The United States of America as represented by the Secretary of the Army, Washington, D.C.

[21] Appl. No.: 580,496

[22] Filed: Feb. 15, 1984

[51] Int. Cl.$^4$ .............................................. C07C 37/02
[52] U.S. Cl. ........................................ 514/8; 424/22; 514/965; 514/953
[58] Field of Search ................... 260/112.5 R; 424/22; 424/177

[56] References Cited

U.S. PATENT DOCUMENTS

| | | | |
|---|---|---|---|
| 3,773,919 | 11/1973 | Baswell et al. | 424/78 |
| 3,887,699 | 6/1975 | Yolles | 424/19 |
| 3,976,071 | 8/1976 | Sadek | 424/22 |

OTHER PUBLICATIONS

Hollinger, Jeffrey O., Biomat., Med. Dev., Art. Org., 10(2), pp. 71–83 (1982).
Hollinger, Jeffrey O., Journal of Biomedical Materials Research, vol. 17, pp. 71–82 (1983).

*Primary Examiner*—Delbert R. Phillips
*Assistant Examiner*—F. T. Moezie
*Attorney, Agent, or Firm*—John H. Raubitschek; Arthur I. Spechler; Werten F. W. Bellamy

[57] ABSTRACT

A novel material consisting of a combination of a proteolipid and biodegradable, biocompatible copolymer has been developed for improving and accelerating the healing of osseous tissue. The proteolipid was prepared by combining muco-peptide-N-acetyl-muramoylhydrolase with phosphatidyl inositol, 4,5-diphosphate and the copolymer consists essentially of a 50:50 poly(L)(−)lactide co-glycolide.

4 Claims, 10 Drawing Figures

POLYLACTIC-POLYGLYCOLIC ACIDS COMBINED WITH AN ACIDIC PHOSPHOLIPID-LYSOZYME COMPLEX FOR HEALING OSSEOUS TISSUE

BACKGROUND OF THE INVENTION

An extremely challenging orthopedic task has been the architectural reconstruction of osseous defects which may have been a sequela of infection induced bony sequestration, developmental malformation, surgical resection, or traumatic avulsion. The need to initiate repair and to restore structurally deficient bone has inspired the development and application of a bewildering array of materials.

Autogeneic and allogeneic agents have been employed for orthopedic and maxillofacial skeletal procedures. However, an overall failure rate of 13-30% for autografts and even greater failure rate for allografts and alloimplants militate against unequivocal, universal acceptance of these materials for bone repair and replacement. Preparation of xenogeneic substances by current methods for human application is considered to be unacceptable. See for example, Urist, M. R., *Fundamental and Clinical Bone Physiology*, pp. 331-368, (1981).

Bone derivatives (i.e., demineralized bone), collagen gels, and ceramics of various stoichiometries have been investigated for osseous repair and augmentation. Antigenicity and the diversity and unpredictability of the host rsponses to these agents have precluded immediate clinical application.

Investigators have used biodegradable bone plates and screws prepared from the homopolymer polylactic acid (PLA) to repair and stabilize mandibular and orbital features. After 32-36 weeks these devices were still detectable microscopically, and although biocompatibility, osseous healing, and osteoconduction were evident at the repair sites, the slow biodegradation of the PLA may be considered a deterrent to bone healing. Applicant fabricated a copolymer of polylactic acid (PLA) and polyglycolic acid (PGA) that had significantly different chemical and physical properties from the PLA homopolymer. Experimental evidence suggested that the copolymer formulation might be osteoconductive and osteoinductive.

A basic protein-acidic phospholipid complex that has been isolated from Bacterionema matruchotii has been shown to induce hydroxyapatite formation in vitro. A similar proteolipid consisting of mucopeptide-N-acetylmuramoylhydrolase and phosphatidyl inositol 4,5-diphosphate has been tested in vivo and evaluated histomorphometrically by applicant. It was determined that the rate of bone formation was more rapid at sites treated with this agent than at non-treated control sites.

The proteolipid in the form investigated by applicant has a paste-like consistency. This physical attribute is usually not satisfactory for repairing many types of osseous defects. Preliminary studies revealed that when the PLA:PGA copolymer is in a doughy state it may be combined with the proteolipid. After curing, a rigid, porous, and bone-like material can be produced that can be carved into any desired shape.

Applicant has discovered that a copolymer of PLA:PGA combined with a proteolipid will facilitate improved healing of osseous wounds. The evaluation of applicant's findings was accomplished by quantitating elements of bone repair (i.e., cellular, osteoid, trabeculae) using computer assisted histomorphometric analysis of selectively stained specimens obtained from osseous wounds treated with the copolymer-proteolipid material.

The ultimate objective of applicant's investigation was to promote the development of a bone repair and replacement compound that will be immunologically acceptable; nontoxic; commensurate in physical properties to bone; osteoconductive; osteoinductive; replaceable at controlled and predictable rates by osseous tissue; readily available; easily and conveniently shaped; suitable for rigid fixation; and esthetically and functionally capable of integrating with existing anatomical structures.

SUMMARY OF THE INVENTION

This invention relates to a novel composition and method for improving and promoting the healing of osseous tissue which comprises implanting at the site of the broken osseous tissue a therapeutically-effective amount of a composition comprising a proteolipid incorporated into a biodegradable polymeric matrix. More precisely, applicant's invention is directed to a novel formulation comprising a proteolipid such as mucopeptide-N-acetylmuramoylhydrolase:phosphatidyl inositol 4,5-diphosphate incorporated in a copolymer of poly(L)(—)lactide co-glycolide polymeric matrix which is implanted at the site of the broken osseous tissue to improve and promote the healing of said tissue. Applicant has found that the composition which is especially preferred consists essentially of a copolymer of 50:50 poly(L)(—)lactide co-glycolide and the proteolipid, mucopeptide-N-acetylmuramoylhydrolase:phosphatidyl inositol 4,5-diphosphate in an amount of about 1 to 5 percent, preferably 1%, by weight the copolymer.

Materials such as bone grafts and implants, collagen gels, ceramics, bone derivatives, and biopolymers are some of the many agents which have been employed by orthopedic and maxillofacial surgeons for initiating osseous repair or for replacing bone. Failure to achieve beneficial results with these materials has not been necessarily a consequence of imprudence; but rather, due to deficiencies inherent to the repair and replacement agents. Surprisingly, applicant has discovered that a combination of the biopolymers polylactic acid (PLA) and polyglycolic acid (PGA) in conjunction with a particular proteolipid (mucopeptide-N-acetylmuramoylhydrolase:phosphatidyl inositol 4,5-diphosphate) represents a significant improvement over conventional materials.

Homopolymers and copolymers of PLA and PGA have been used to manufacture biodegradable suture material. Different formulations of these same biopolymers also have been used experimentally for osseous repair and reconstructive procedures.

An important aspect of evaluating biopolymers involves characterization of their degradation properties. Kulkarni et al. described in the Journal of Biomedical Mater. Res., Vol. 5, pp. 169-181, (1971) a study of the homopolymer PLA using a $^{14}C$-label. They compared breakdown kinetics of D,L- and L-isomers and they established that the D,L-isomer degraded more rapidly. It has been determined by histological methods, that cylinders of homopolymers of either PLA or PGA persisted in situ for 220 days or more, whereas a copolymer with a ratio of 25 PLA:75 PGA degraded most rapidly (approximately 100 days), followed in succession by 50 PLA:50 PGA and 75 PLA:25 PGA. Bone plates and retaining screws were fabricated from PLA and have been used to repair mandibular fractures in dogs and blowout fractures of the orbital floor of monkeys. The PLA showed histological evidence of biodegradation and peripheral fragmentation by six weeks; however, the PLA was still detected at the repair sites 32-38 weeks following insertion. Investigators have reported that osseous healing appeared to be progressing satisfactorily despite the polymer's presence. Nelson et al. reported in *Oral Surg;* Vol. 43, pp. 836-843, (1977) a histolotical evaluation of the copolymers of PLA:PGA combined with a ceramic material to determine if this combination was osteogenic. They suggested that these agents were osteoconductive but not osteoinductive. Applicant inserted bone implant plugs consisting of 50 PLA:50 PGA into orthotopic sites and reported evidence of initial degradation at three days. Osseous repair was quantitated by computer assisted histomorphometric analysis and it was determined that bone reparative elements were in greater abundance and were present earlier in osseous wounds treated with 50 PLA:50 PGA implants than compared with untreated control sites.

It is apparent from reviewing the literature that a diversity of results exists concerning degradation rates, mechanical and physical properties, and the in situ effects of the biopolymers PLA and PGA. It appears that composition ratios of the constituent homopolymers and their characteristic crystallinity and optical activity are important determinants of the observed properties of biopolymers. Different preparation techniques for fabrication of these agents can result in products with startlingly unusual physical and chemical characteristics. A hard, porous design was selected by applicant for the implants used in because it is favored for rigid, stable bone fixation, and it also permits a greater surface area for degradation by hydrolytic scission and subsequent osseous ingress.

Autografts are the favored treatment for bone repair and replacement used by orthopedic and maxillofacial surgeons. However, inability to recover sufficient autogenous bone, technical inconvenience, and patient trauma from a second surgical procedure are some of the problems associated with autografts. The potentially unlimited supply of the copolymer-proteolipid that can be synthesized in the laboratory, and the characteristic of being easily carved into any geometry by the surgeon, are distinct advantages that this material possess over the more commonly employed repair and reconstruction agents.

Biodegradation of homopolymers and copolymers of PLA and PGA occurs by a process of nonspecific hydrolytic scission that results in the generation of lactic acid and glycolic acid residues. The lactic acid becomes incorporated in the tricarboxylic acid cycle and is excreted by the lungs as carbon dioxide. The glycolic acid dimers, trimers, etc., are enzymatically degraded by esterases and carboxypeptidases and are converted to monomers of glycolic acid which either can be excreted in the urine or enzymatically converted by glycolate oxidase to glyoxylate. This moiety reacts with glycine transaminase and the glycine that is produced can be used for the synthesis of serine, which can be employed in the tricarboxylic acid cycle after transformation into pyruvate.

Extremely important requirements for a bone repair and replacement material are tissue tolerance and lack of immunogenicity. Biopolymers consisting of PLA and PGA have been evaluated in both hard and soft tissues, and there is unequivocal evidence of host tissue acceptance. No adverse tissue reactions were observed histologically by applicant. Long term, single dose acceptance of PLA by host tissue has been reported.

Neutrophils were detected in the early phases of applicant's investigation; however, these cells were considered to be a component of the normal inflammatory response associated with healing, rather than with being part of an immunologic phenomenon of host rejection. Failures (i.e., host-graft rejection) associated with various types of bone grafts and implants, and protein derived bone replacement substances (i.e., collagen), frequently are caused by an immunologic response engendered by the foreign material. The immunologic response is typically manifested as an overwhelming cellular infiltrate of neutrophils (acute phase) and eventually lymphocytes and plasma cells associated with the chronic phase become prevalent.

Considerable attention has been focused on the important role that certain acidic phospholipids perform in the process of calcification. Several investigators have suggested that acidic phospholipids possess both calcium binding capacity and a strong affinity for intramembraneous proteins. A proteolipid complex consisting of a basic protein-acidic phospholipid has been shown to be capable of initiating calcification in vitro. In prior experiments, applicant has prepared a proteolipid composed of a lysozyme (mucopeptide-N-acetylmuramoylhydrolase) and an acidic phospholipid (phosphatidyl inositol 4,5-diphosphate). This material was implanted into bony wounds in experimental animals and the healing response was evaluated by computer assisted histomorphometric methods. Initial healing rates for the proteolipid treated wounds exceeded the control sites which suggested to applicant that the proteolipid established a special (chemical) environment conducive to calcium and phosphate precipitation, nucleation, and subsequent crystal growth. The implication was that this substance was tantamount to surrogate extracellular matrix vesicles, the structures whose limiting membrane is heavily endowed with an acidic phospholipid component.

Applicant did not observe any adverse tissue reactions or an unusual inflammatory response in the experimental animals that had been treated with the proteolipid. The combination of the copolymer and proteolipid used in the practice of this invention was tissue tolerant. It appears, therefore, that such a compound could be considered nonimmunogenic.

The formulation of the proteolipid employed by applicant has a paste-like consistency that is unsatisfactory for bony wound application when rigid fixation is required or when expansive discontinuity defects must be repaired. Hence, an appropriate vehicle or delivery system for the proteolipid had to be conceived. Applicant selected the biodegradable, biocompatible copolymer of 50 PLA:50 PGA. The copolymer is amenable to a wide variety of shapes. Many degradation rates can be managed merely by altering component ratios and crystallinity. Numerous types of density characteristics also can be devised in the laboratory. When the appropriate size, shape, and physical properties of the carrier (copolymer) are determined, the proteolipid can be incorporated into the raw polymer. During the process of copolymer biodegradation the proteolipid component is released into the local environment milieu. This concept was the impetus behind the development of the combination of 50 PLA:50 PGA plus proteolipid that was evaluated. However, before this material was assessed, each component was evaluated on its own merit. There had not been any reports in the literature until applicant described an in vivo bone repair application of the proteolipid selected for this study in *Biomat. Med. Dev. Art. Org.*, Vol. 10(2), pp. 71–83, 1982. Additionally, the physical and chemical characteristics of the copolymer that were evaluated by applicant in *J. Biomed. Mater. Rev.*, Vol. 17, pp. 71–82, 1983 had not been previously reported. Prior to applicant's invention, it was not known what the effects would be of combining the proteolipid and the copolymer. The histomorphometric analysis of the implant sites where the combination material was employed, indicated that it performed extremely well in inducing early phases of osseous wound healing. Histological examination revealed that the combination material was osteoconductive and non-immunogenic.

The initial periods (days three, seven, and fourteen) of histological observation revealed an abundance of swirls of connective tissue and fibroblast-like cells in groups A (copolymer-proteolipid) and B (copolymer). The discernable quantitative increase of collagenous fiber material in group A as compared to Group C, could explain the more rapid formation of bone wound healing elements produced at the implant site. Collagen fibers perform an important role in the process of mineralization. This is based on the concept that tropocollagen's singularly unique physical and chemical properties cause deposition of calcium and phosphate into the pores between adjacent linear and colinear molecules. It is certainly possible that the configurational array of the fibrous swirls of collagen at days three, seven, and fourteen were in some manner responsible for hastening bone repair at the implant areas. The untreated wounds did display histological features similar to groups A and B, although the quantity of osseous healing elements was significantly less than in the implant treated sites and the fibrous connective tissue component appeared to be scantier.

Applicant is aware of features described by other investigators, such as a cellular inflammatory phase of healing, fibroblast proliferation, and ultimately implant incorporation. However, in experiments where a variety of bone repair, replacement, and augmentation procedures were performed, the extensive masses of connective tissue initially observed by applicant at the healing sites had not been reported elsewhere.

TABLE I

| Variables | Tx | Day-3 | Day-7 | Day-14 | Day-21 | Day-28 | Day-42 |
|---|---|---|---|---|---|---|---|
| VV | A | 104.57 | 179.93 | 290.37 | 360.06 | 356.93 | 410.07 |
|  | B | 085.92 | 156.52 | 200.39 | 268.68 | 303.01 | 364.56 |
|  | C | 044.81 | 100.87 | 136.70 | 228.99 | 276.53 | 371.01 |
| D-TRAB | A | 017.58 | 028.91 | 047.14 | 070.97 | 085.84 | 164.03 |
|  | B | 011.53 | 019.29 | 028.01 | 046.22 | 066.73 | 151.58 |
|  | C | 009.27 | 011.35 | 015.70 | 026.65 | 050.26 | 134.49 |
| TH-OS | A | 006.27 | 010.80 | 018.53 | 022.80 | 030.30 | 038.75 |
|  | B | 005.01 | 009.21 | 012.40 | 020.87 | 028.11 | 035.43 |
|  | C | 002.92 | 003.96 | 008.37 | 013.65 | 018.60 | 031.19 |
| VV-OS | A | 001.68 | 003.76 | 006.59 | 007.66 | 009.94 | 012.03 |
|  | B | 001.81 | 003.19 | 003.67 | 007.89 | 008.28 | 011.54 |
|  | C | 001.22 | 001.42 | 003.69 | 005.75 | 008.36 | 010.15 |
| OBI | A | 034.79 | 056.70 | 090.85 | 143.40 | 237.85 | 285.87 |
|  | B | 036.12 | 051.93 | 085.52 | 126.18 | 212.41 | 267.80 |
|  | C | 028.58 | 047.36 | 077.13 | 089.74 | 134.42 | 218.06 |
| OB % | A | 007.98 | 014.20 | 032.15 | 048.27 | 051.01 | 044.73 |
|  | B | 007.80 | 014.55 | 027.66 | 038.26 | 049.88 | 048.58 |
|  | C | 005.18 | 010.52 | 020.21 | 033.87 | 040.48 | 046.06 |
| L-TO1% | A | 000.60 | 006.24 | 013.08 | 012.29 | 007.71 | 006.37 |
|  | B | 000.66 | 006.26 | 011.69 | 012.31 | 007.50 | 005.46 |
|  | C | 000.65 | 006.56 | 011.20 | 012.05 | 008.21 | 005.88 |

Tx: represents treatment.
A = copolymer plus proteolipid; B = copolymer; C = control.
Each value represents the pooled mean of 2,000 measurements.

The histomorphometric measurements appearing in TABLE I enabled additional quantitative information about bone to be derived as a consequence of the programmed algorithms of the computer. A total of seven variables, therefore, were selected for statistical assessment.

1. Volumetric density of bone: trabecular bone/volume of total bone, in $mm^3/cm^3$. (VV).
2. Mean trabecular diameter, in micrometers. (D-TRAB).
3. Mean width of osteoid, in micrometers. (TH-OS).
4. Volumetric density of osteoid: volume of osteoid/volume of total bone, in $mm^3/cm^3$. (VV-OS).
5. Osteoblast index: number of osteoblasts/10 cm of trabecular bone length, in number/10 cm. (OBI).
6. Fraction of total trabecular surface covered by osteoid, in %. (OB%).
7. Fraction of trabecular surface exhibiting resorptive lacunae, in %. (L-TOT%).

TABLE II

Organization of Data for the Variable Trabecular Diameter (D-TRAB)
from Treatment Group A, Temporal Group 3 Days

| Number of animals | Pooled number of fields per animal |
|---|---|
| 10 | 200 |

| Total number of fields/set | | Possible number (range) of variables |
|---|---|---|
| 2,000 | ↓ | 1–9 |
|  | ↓ 2,000 measurements of D-TRAB per set $A_3$ | Trabecular diameter in $\mu m$ |
|  | ↓ | Computer derivation of standard deviation (A) for D-Trab |
| Result – $A_3$ | ↓ | D-TRAB ± s |

Key:
T = Temporal group (3, 7, 14, etc.) in days
Tx = Treatment group (A, B, C)
Set = (Tx) (T) = $A_3$, $B_3$, $C_3$, $A_7$, etc.
s = Standard deviation

TABLE III

Example of Possible Number of Variables from Treatment Groups A, B, and C

| Temporal groups (T) in days | 3 | 7 | 14 | 21 | 28 | 42 | Grand Total |
|---|---|---|---|---|---|---|---|
| Pooled number of fields | 200 | 200 | 200 | 200 | 200 | 200 | |
| Number of animals per T | 10 | 10 | 10 | 10 | 10 | 10 | |
| Total number of fields | 2,000 | 2,000 | 2,000 | 2,000 | 2,000 | 2,000 | 12,000 |

Explanation:
1. There were ten animals per temporal group (T).
2. There were 200 fields measured per animal; therefore, 2,000 fields were measured per T (200 × 10 = 2,000).
3. The possible range of derived variables was from one to nine with a mean of five; therefore, 10,000 pieces of information could be computed per T (2,000 × 5 = 10,000).
4. The term set can be defined as a treatment group (Tx) at a particular time (that is, a T of 3, 7, 14, 21, 28, or 42).
5. A grand total (average) of 180,000 measured values could, therefore, be derived (10,000 × 18 = 180,000).

STATISTICAL ANALYSIS OF THE HISTOMORPHOMETRIC DATA

Histomorphometric data were generated by measuring 50 fields from each of four histologic slides prepared from either control or experimental sites from each animal. A total of 200 fields per animal were analyzed. Data from the analyses of the same variable from the same temporal and treatment groups were combined, yielding a pooled mean value based upon 2,000 measurements (TABLE II). (An overview of possible data generation may be seen in TABLE III.) A standard deviation and a standard error of the mean were computed for each set of 2,000 measurements for each set of 2,000 measurements for each variable according to the formulae (Dunn, *Basic Statistics: A Primer for the Biomedical Sciences*, pp. 38–44, 1967; Sokal and Rohlf; *Biometry*, pp. 57–62, 1969):

$$\text{Standard deviation } (s) = \sqrt{\frac{\Sigma(X - \overline{X})^2}{n - 1}}$$

where
X = the pooled values for 2,000 measurements
$\overline{X}$ = the mean
n = the sample size $$\text{Standard error of the mean } (se(\overline{X})) = \frac{s}{\sqrt{n}}$$

The pooled mean for each variable (based upon 2,000 fields) plus and minus its standard error of the mean was then used to construct a histogram. A trio of sets (i.e., $A_3$, $B_3$, $C_3$) representing treatment and temporal groups were arranged along the abscissa and the corresponding units or percentage appeared along the ordinate.

A two-way analysis of variance computer program was used to examine and to test the effects of (1) the treatment groups (differences between the three treatment groups analyzed over the six time periods) and (2) time periods (differences between the six time periods averaged over the three treatment groups). Effects having an observed significance level (p-value) equal to or less than 5% (based on the appropriate F-test value which was derived by performing the two-way analysis of variance) were considered to be statistically significant. Differences between the pooled means of any two treatment groups were tested by partitioning the overall difference between treatment group variability, with variability being equivalent to the sum of squares that was calculated by using the computer program. Specific comparisons were then made between treatments. This procedure is tantamount to using a t-test to compare any two treatment means per temporal group (Box et al., *Statistics for Experiments*, pp. 208–244, 1978).

As shown in the histograms depicted by FIGS. 1 to 7, all treatment groups appeared to display the typical patterns of osseous wound healing. There was often some evidence that histologically evaluated wound healing might have been superior for one type of treatment class than in another; however, when histomorphometric assessment and statistical analyses were performed, contrasts were extracted that frequently proved to be significantly different.

Overall, histological evaluation seemed to indicate that the pattern of healing consisted of more reparative elements in the copolymer-proteolipid (A) treated sites at an earlier period in time than either the plain copolymer (B) or control (C) sites. It did not appear that the presence of the implants deterred bony healing, which was occurring in a progressive manner from the peripheral aspects of the wound and towards the center. Fibrous elements and fibroblast-like cells were more common in the implant treated sites than in the controls.

Histomorphological quantitation of the copolymer-proteolipid treated wounds revealed to applicant that these sites did heal more rapidly than the control wounds or plain copolymer treated wounds.

The fact that treatment contrasts between groups A and B were noted at the same temporal periods, adds credence to the important contribution of the proteolipid to osseous healing (TABLE I).

The relationship previously described between osteoblast index and the amount of reparative elements measured was consistent until day 21. From day 21 to day 42 the number of osteoblasts demonstrated a greater numerical contrast than at earlier period (TABLE I, FIG. 5). However, the mean bone volume and trabecular diameter did not display commensurate variances (TABLE I, FIGS. 1 and 2). The stimulatory affect that the implant had on the osteoblasts could have been assuaged by day 21, at which time normal reparative processes at the control sites were more active than at earlier periods. The apparent early effect at hastening wound repair was achieved with the implants, followed by a more subdued tissue response at later stages.

The computations involved in deriving the statistical plots of the histomorphometric variables confirm the observations that have been described. When reparative elements developed rapidly, the progress over time could be defined according to an equation with a strict linear component. However, as those elements began to decrease in quantity, the progress was defined by a quadratic equation, and its graphic plot would be a curve. Depending upon the histomorphometric data accrued, that plot might have had a cubic or quartic component. The linear plot modified by a quadratic component, for example, might indicate that an initial burst of activity had been followed by a more subdued healing response (i.e., FIG. 1, the plot for group A).

The benefits of wound repair studies have been advanced tremendously by the application of the computer and the image analysis system. An important demonstration of this point is the relationship developed between FIG. 1 (volumetric density of bone), FIG. 6 (osteoclast index), and FIG. 7 (total resorptive lacunae). The significance of this relationship helps to emphasize the invaluable assistance that histomorphometric quantitation confers on a bone wound repair study. Conventional histological methods could confirm the histomorphometric assessment that overall, there was no difference between osteoclast morphology and number from the different treatment groups. If the histomorphometric data from FIGS. 1, 6, and 7 were integrated, it would become obvious that overall osteoclastic activity at the implant treated wounds intensified from day three until day fourteen. This fact is evident because the expected effect for L-TOT % (FIG. 7) should have been that C was greater than B, which was greater than A. The trend was just the converse, where A was greater than B, which was greater than C. Furthermore, VV (FIG. 1) demonstrated consistently that A was greater than B, which was greater than C.

The combination of animal model and experimental wound site and its size may have contributed to a particular piezoelectric effect that caused bone deposition rather than cartilage formation, even during the initial phase of repair. The absence of cartilage formation at a wound site is a beneficial effect of the implant material, because cartilage deposition and its subsequent remodelling can be considered as factors that delay the final stage of repair of osseous elements.

It has been demonstrated that the mode of fixation (rigid vs. flexible) is an important influencing factor for callus development.

Applicant has observed that the copolymer-proteolipid material used in the practice of this invention was tissue tolerant and that at experimental wounds the elements of bony repair formed earlier and in greater quantity than at nontreated sites. Additionally, freeing of the proteolipid by the biodegrading copolymer could contribute to the more rapid accumulation of the calcium and phosphate ions needed for formation of bone reparative elements. The addition of the proteolipid further enhanced the action of the copolymer because of its proposed role as a calcification inducer, tantamount to the function of the matrix vesicle. The absence of cartilage and callus formation was evident at all three types of treatment sites. It is advantageous that neither cartilage nor a callus developed, because such products could impede the rate at which bony union is achieved. The biocompatibility of the copolymer-proteolipid implants were demonstrated histologically. Accessibility and the capability to be shaped into any desired geometry are additional benefits offered by the copolymer-proteolipid material.

EXAMPLES

The herein offered examples provide methods for illustrating, without any implied limitation, the practice of this invention in the treatment of osseous wounds.

The profile of experiments have been chosen to illustrate the osseous tissue healing activity of the copolymer-proteolipid composites. Applicant prefers to use a copolymer of poly(L)(-)lactide co-glycolide as the polymeric matrix.

All temperatures not otherwise indicated are in degrees Celsius (°.) and parts or percentages are given by weight.

MATERIALS AND METHODS

A. Animals

One hundred eighty adult Walter Reed Strain of rats (random male and female) weighing between 250-300 grams each, were obtained. Animals were segregated by sex and assigned in groups of three to polycarbonate cages fitted with stainless steel wire covers and mesh floors. A large metal tray was below the wire mesh floor to catch waste products.

The rats were kept in a controlled environment of 33° C. with 12-hour periods of light and dark. Cages and metal trays were cleaned five times per week. Purina Rat Chow ® and water were provided ad libitum.

Before the experiment was initiated, a period of two weeks was allowed for the rats to become acclimated.

B. Preparation of the implants

1. Lysozyme

A commercially manufactured lysozyme (mucopeptide-N-acetyl-muramoylhydrolase, E. C. #3.2.1.17, three times crystallized, dialyzed, lyophilized) having a molecular weight of 13,000 Daltons was purchased from the Sigma Chemical Corporation.

2. Diphosphoinositide

A commercially prepared diphosphoinositide (phospholipid: phosphatidyl inositol 4,5-diphosphate) having a molecular weight of 1,000 Daltons was obtained.

EXAMPLE 1

Proteolipid

Figure 8:
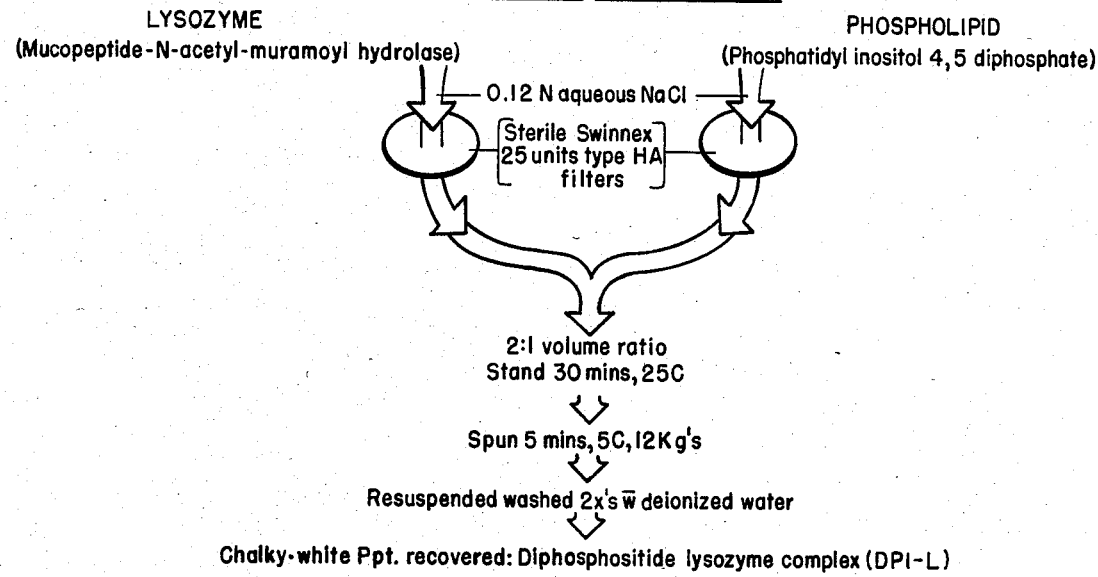

The lysozyme and diphosphoinositide (phospholipid) were dissolved separately in 0.12 N aqueous sodium chloride at a concentration of 1 mg/ml. Each solution was filtered through sterile Swinnex-25 units with type HA filters and the lysozyme solution was titrated with the phospholipid solution until a chalky white precipitate was produced. The volume ratio of lysozyme to phospholipid was approximately 2:1. After standing for 30 minutes at 25° C., the lysozyme-diphosphoinositide solution was spun at 12,000 g in a centrifuge for 5 minutes at 5° C. The precipitate that was recovered was resuspended, washed two times with deionized water, and placed in a lyophilizing chamber for 48 hours at 5 millitorr and −40° C. (FIG. 8). After the proteolipid was removed from the lyophilizing chamber, it was maintained at ambient temperature for 60 minutes, weighed, and the percent yield was determined. The proteolipid was then stored in a tightly sealed tube until it was needed.

EXAMPLE 2

Copolymer

Figure 9:
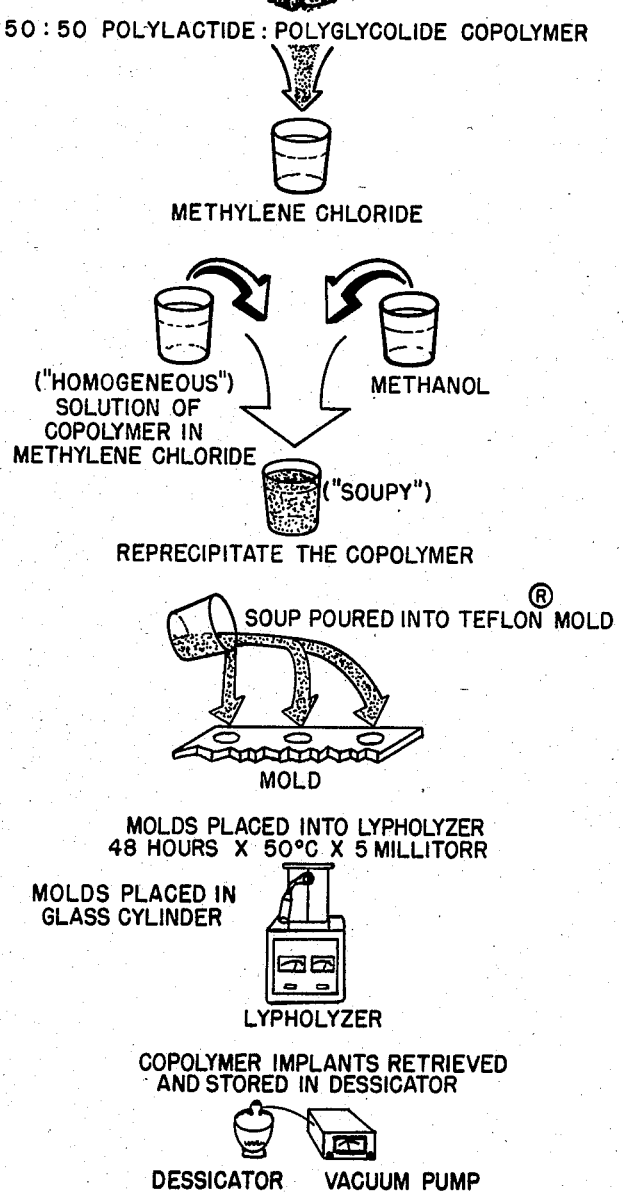

A commercially synthesized copolymer 50:50 poly(L)(−) lactide co-glycolide (50:50 PLA:PGA), having a viscosity of 0.92 dl/g as determined in 1,1,1,3,3,3-hexafluoroisopropanol at 30° C., with a weight-average-molecular weight of approximately 80,000 Daltons, was solubilized in methylene chloride at a 1:12.5 weight:volume ratio. Anhydrous methanol was added to the liquid suspension in a 1:1 volume ratio to precipitate a milky-white gelatinous mass which was blotted between two pieces of sterile #50 Whatman filter paper. The viscous, milky-white copolymer mass was gently forced into prepared wells (2.0 mm × 1.25 mm) of a Teflon mold using a supple Teflon spatula. The mold was then placed in a lyophilizer chamber at 50° C., 5 millitorr, for 48 hours. After removing the Teflon mold from the lyophilizer chamber and waiting 60 minutes, the copolymer was retrieved, and each copolymer implant plug was trimmed and weighed. One hundred and forty 2.0 mm×1.25 mm copolymer plugs weighing approximately 0.711±0.11 gms were prepared in the fashion described. Sterilization was accomplished by using ethylene oxide, 4-5 psi, 30° C., for six hours. Following sterilization, the implant plugs were stored in a desiccator at ambient temperature until they were needed (FIG. 9).

EXAMPLE 3

Copolymer-proteolipids

Figure 10:
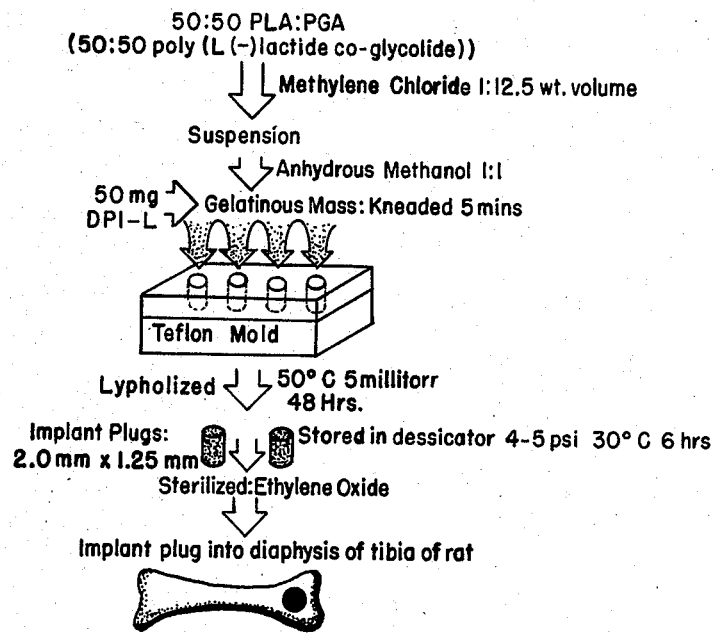

This copolymer was prepared in the manner previously described; however, after the 50:50 PLA:PGA was dried between the sterile #50 Whatman filter paper, a known weight of the previously prepared proteolipid was added. The doughy nature of the copolymer permitted complete incorporating of the proteolipid after five minutes of kneading. The resulting mixture was then placed into prepared wells (2.0 mm×1.25 mm) in a Teflon mold and was treated as already outlined. Before ethylene oxide sterilization, each of the one hundred and forty implant plugs was weighed, and the average weight was determined to be 0.719±0.17 gms. This represented 1% by weight of proteolipid to copolymer. After sterilization, the implants were stored in a desiccator at ambient temperature until they were needed (FIG. 10).

EXAMPLE 4

Preparation of the experimental animals

Sodium pentobarbital, USP at a dosage of 3 to 5 mg/100 g of body weight was administered intraperitoneally for anesthesia. When suitable anesthesia was achieved, the implant and control sites were prepared.

1. Treatment groups

The 180 rats were divided evenly into three groups. One group received the copolymer-proteolipid implant (Group A); the second group received the copolymer implant (Group B); the third group (Group C) served as a control group.

2. Location of the experimental and control sites

The diaphysis of the right and left tibias were selected as the implant and control sites. Each experimental animal received an implant in both tibias; whereas the control group of animals had holes prepared in the tibias but received no implants.

EXAMPLE 5

Preparation of the experimental and control sites

Areas over the experimental and control sites were shaved and scrubbed with providone iodine, N.F. (Betadine®) for five minutes. Using an aseptic technique, a #15 surgical blade was used to make an incision 1 cm in length on the anterolateral surface of each tibia. Soft tissue was carefully dissected and reflected; periosteum was removed, and the broadest area of the diaphysis of each tibia was visualized. A circular hole was prepared completely through the cortical plate and into the medullary cavity using a sterile bone trephine and sterile water coolant. A total of 120 copolymer proteolipid implants were inserted into the appropriate group. The second group of 60 animals received a total of 120 copolymer implants. The control group, also consisting of 60 animals, did not receive any implants in the prepared holes. These sites were left void to heal by normal physiologic means. All surgical sites were closed in layers: 000 Dexon for muscle; 000 silk for skin. After surgery, each animal was identified with both a numbered metal eartag and a number written with picric acid on its back. Animals were returned to their appropriately designated cages.

EXAMPLE 6

Temporal groups

At 3, 7, 14, 21, 28, and 42 days post-treatment, 10 animals from each treatment group were sacrificed by an intraperitoneal administration of sodium pentobarbital, USP (TABLE II).

EXAMPLE 7

Tissue preparation: histomorphometry

Using an aspetic technique, the right tibias were selected for histomorphometric evaluation. A convenient and relatively simple method for retrieving the tibias consisted of preparing an approximately 2 to 3 mm long incision, down to bone, at the level of the femur-tibia articulation. Firmly grasping the deceased animal and pushing caudally-cephalically from the animal's foot with a slight twist, the tibia-fibula complex was cleanly forced through the prepared incision. The bones retrieved in this manner were virtually free of adherent soft tissue. Soft tissue that was present was easily, expeditiously removed with either a sterile 2×2 gauze pad or with an Allis tissue pick-up. The fibula was separated from the tibia. A Hall drill and water coolant were used to section the area of the implant and control site free from the host tibia. At least three to five mm of contiguous host bone encompassed the experimental or control sites. The tissue specimen was immediately placed into its own properly identified vial or specimen holder to obviate specimen confusion. The following procedure was adopted from Villanueva et al., *Am. J. Med. Technol,* Vol. 43, pp. 2 to 5, (1977; *J. Histotech,* Vol. 2, pp. 22-24, 1979) for tissue preparation for histomorphometry.

1. Fixation

Specimens were removed from their marked vials and were inserted individually into properly identified tissue holders. Specimens were placed en masse into large glass jars which were filled with 70% ethanol. A magnetic stirring bar was inserted and the jars were sealed. Specimens were maintained in this fashion for 24 hours at ambient temperature while constantly being stirred on a magnetic stirrer.

2. Dehydration

Still within their individually marked tissue holders, the 70% ethanol was evacuated from the jars and new 100% ethanol was added, and this was stirred constantly at ambient temperature. This procedure was performed five times at 24-hour intervals.

3. Absolute (100%) ethanol plus methylmethacrylate

The 100% ethanol was removed from the jars and a 50/50 (v/v) solution of 100% ethanol: methylmethacrylate was added. This was stirred constantly with a magnetic stirrer at room temperature for 24 hours.

4. Methylmethacrylate

The 50/50 solution was removed from the jars and it was replaced by 100% methylmethacrylate. Each glass jar was then placed inside a vacuum chamber (15 psi) which was put on a magnetic stirrer and the specimens were stirred constantly at room temperature for 24 hours. This procedure was repeated twice and the methylmethacrylate was changed each time.

5. Polymerization solution

The polymerization solution was prepared as follows:
a. 100 ml of methylmethacrylate
b. 30 ml of Plastoid N ® (Rhome Pharmica)
c. 3 gms of benzoyl peroxide The ingredients were combined and the mixture was stirred approximately 20 minutes until the benzoyl peroxide was completely dissolved and the solution appeared homogenous. Tissue specimens were removed from the tissue holders and they were placed individually into appropriately identified screw-topped scintillation vials that were filled with seven milliliters of polymerization solution. Vials were then placed into a refrigerator at 5° C. for 24 hours. After 24 hours the polymerization solution was replaced with fresh solution, and the vials were treated as previously described. The cycle was repeated once again, except the third time the vials were placed in a water bath for 24 hours at 48° C. After 24 hours the vials were removed from the water bath, the tops were unscrewed, and two milliliters of 100% ethanol was added to allow for completion of surface polymerization which was achieved after one to two hours.

6. Handling of the embedded specimen

The vials were broken with a small hammer and a cylinder of polymerized methacrylate containing the embedded specimen was retrieved. The appropriate identification number was then inscribed on the side of each cylinder using a diamond tipped marking pen. The excess methacrylate was judiciously trimmed away from the embedded bone specimen and each trimmed cylinder was placed into the specimen holder of an LKB-Historange. An 18 cm Shandon tungsten-carbide knife with a K-profile was set at 5° in the knife stage and was used for fine trimming. Specimen sections that were retained for examination were cut at 3 $\mu$m.

7. Glass slide preparation

Prior to placing the bone sections onto glass slides they were prepared in the following manner:
a. Each slide was cleaned with a int-free wipe and 100% ethanol, and was placed into a specially prepared gelatin bath for eight minutes at 49° C.
b. After removal from the gelatin bath, slides were placed into Coplin jars that were inserted into a Sorvall GS-3 rotor which was then placed into a Sorvall RC-5 centrifuge and was spun at 2,000 RPM, 25° C. for 15 minutes.
c. Coplin jars were removed from the centrifuge and the slides were allowed to dry at ambient temperature for two hours.
d. Gelatin coated slides were then placed into slide boxes for subsequent use.

8. Gelatin preparation

The gelatin for coating the slides was prepared in the following fashion:
a. Solution #1
(1) 1 l of distilled water heated to 75° C.
(2) 4.5 gms of microbiological gelatin
(3) The components were mixed for 30 minutes until the gelatin was completely dissolved.
b. Solution #2
(1) 5 gms of chromium potassium sulfate
(2) 100 ml of distilled water
(3) The ingredients were mixed for 30 minutes until a completely homogenous solution was achieved.
c. 38.5 ml of solution #2 was added to solution #1 and was stirred for 15 minutes. Glass microscope slides were coated as previously described. The unused volume of gelatin solution was stored in a refrigerator at 5° C. until it was needed.

AREAS OF UTILITY

The results of applicant's evaluation indicate that copolymer-proteolipid implant material was very successful at stimulating the early phases of bone repair and that it can be used as an unexpectedly superior alternative to the agents commonly employed for bone repair and reconstruction. In addition to these areas of utility, the novel copolymer-proteolipid material would be useful for bone fixation and augmentation; in liquid form to cover eroded dental enamel, cementum or dentin, or used to reinforce brittle fingernails or toenails.

I claim:

1. A method for improving and promoting the healing of osseous tissue in an animal which comprises implanting at the site of the broken osseous tissue an effective amount of a biodegradable copolymer-proteolipid material, said material consisting essentially of from 1 to 5 weight percent of the mucopeptide-N-acetyl-muramoylhydrolase:phosphatidyl inositol 4,5-diphosphate, incorporated into from 95 to 99 weight percent of the biodegradable copolymer, 50:50 poly(L)(-)lactide co-glycolide.

2. The method of claim 1 wherein the amount of mucopeptide-N-acetylmuramoylhydrolase:phosphatidyl inositol 4,5-diphosphate is about 1 percent by weight of said copolymer.

3. A pharmaceutical composition useful in improving and promoting the healing of broken osseous tissue comprising an effective amount of from 1-5 weight percent of mucopeptide-N-acetylmuramoylhydrolase:phosphatidyl inositol 4,5-diphosphate incorporated into from 95-99 weight percent of the biodegradable copolymer of 50:50 poly(L)(-)lactide co-glycolide.

4. The composition of claim 3 wherein the amount of mucopeptide-N-acetylmuramoylhydrolase:phosphatidyl inositol 4,5-diphosphate is about 1 percent by weight of said copolymer.

* * * * *